United States Patent
Weiss et al.

(10) Patent No.: US 6,475,484 B1
(45) Date of Patent: Nov. 5, 2002

(54) RECOMBINANT ANTIBACTERIAL GROUP IIA PHOSPHOLIPASE A2 AND METHODS OF USE THEREOF

(75) Inventors: Jerrold Weiss, Coralville, IA (US); Peter Elsbach, New York, NY (US); Ning-Sheng Liang, Nanning (CN)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/740,569

(22) Filed: Dec. 18, 2000

Related U.S. Application Data

(60) Provisional application No. 60/172,467, filed on Dec. 17, 1999.

(51) Int. Cl.[7] .......................... A61K 38/46; C12N 9/14; C12N 1/20
(52) U.S. Cl. .................... 424/94.6; 435/195; 435/253.4
(58) Field of Search .................. 424/94.6; 435/195, 435/253.4

(56) References Cited

U.S. PATENT DOCUMENTS 5,874,079 A    2/1999    Weinrauch et al. ........ 424/94.6

OTHER PUBLICATIONS

Kramer Ruth M. et al. Structure and Properties of a Human Non–pancreatic Phospholipase A2, J. Biol. Chem. 1989, 264, 5768–5775.*
Dennis, J. Biol. Chem. 269: 13057–13060, 1994.
Gelb et al., Ann. Rev. Biochem, 64, 653–688, 1995.
Dennis, Trends Biochem. Sci. 22: 1–2, 1997.
Cupillard, et al., J. Biol. Chem. 272: 15745–15752, 1997.
Wright et al., J. Clin. Invest. 85: 1925–1935, 1990.
Weiss et al., J. Biol. Chem. 269: 26331–26337, 1994.
Elsbach et al., Trends Microbiol. 2: 324–328, 1994.
Madsen et al., Infect. Immune. 64: 2425–2430, 1996.
Weinrauch et al., J. Clin. Invest. 102 (3): 633–638, 1998.
Scott D.L., White, S.P., Browning, J.L., Rosa, J.J., Gelb, M.H., Sigler, P.B. 1997. Science 254: 1007–1010.
Bomalaski et al., J. Immunol. 146: 3904, 1997.
Cirino et al., J. Rheumatol. 21: 824, 1994.
Thannhauser et al., Biochemistry 24: 7681–7688., 1985.
Liang, N.S. et al., FEBS Letters 334: 55–59, 1993.
Fourcade et al., Cell 80: 919–923, 1995.
Hochkeppel et al., *J. Clin. Microbiol,* 25:526–530.
McKenney et al., *Science* 284: 1523–1527.
Xu et al., *Infect. Immun.* 60: 1358–1362; Table I.

* cited by examiner

*Primary Examiner*—Tekchand Saidha
*Assistant Examiner*—Malgorzata A. Walicka
(74) *Attorney, Agent, or Firm*—Darby & Darby

(57) ABSTRACT

Disclose herein is a novel recombinant mutant protein of human Group IIA phospholipase A (PLA2) which has enhanced antibacterial activity when compared to the wild-type human Group IIA PLA2, pharmaceutical formulations comprising the protein and methods of use thereof. Additionally, the formulations may comprise other bioactive compounds, such as, e.g., conventional antibiotics, that act additively or synergistically with Group IIA PLA2 in order to promote bacterial killing.

8 Claims, 13 Drawing Sheets

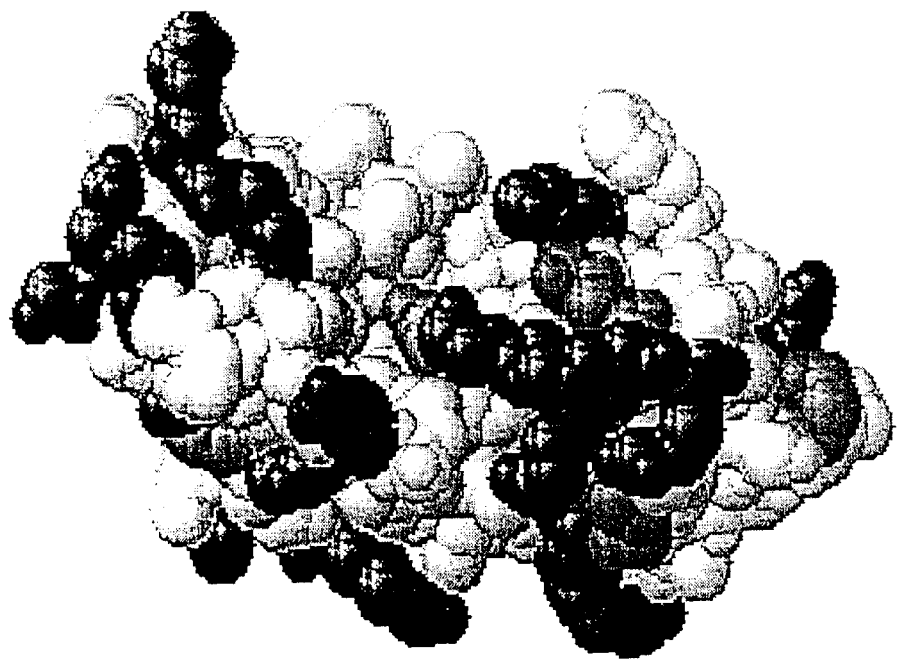
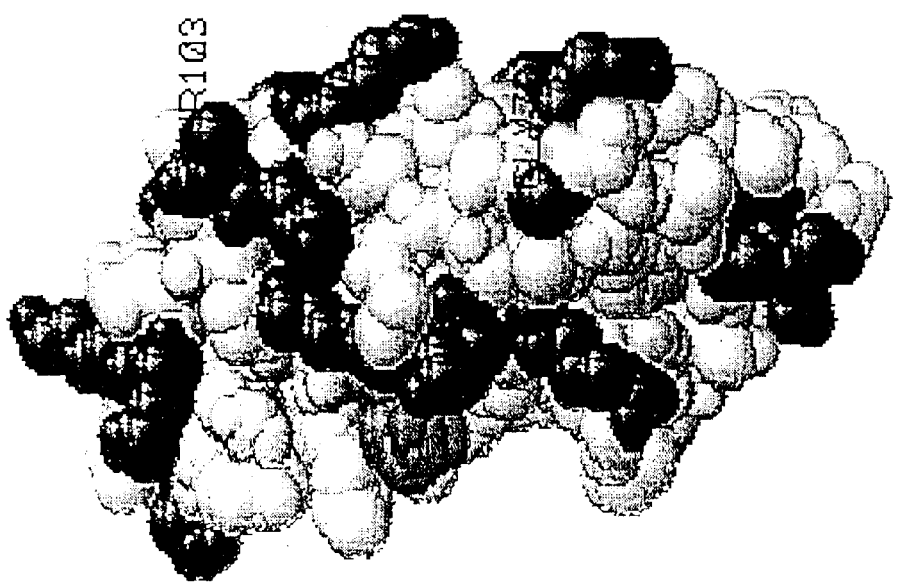
FIG. 1C

FIG. 3A

AAT TTG GTG AAT TTC CAC AGA CTG ATC AAG TTG ACG ACA GGA AAG GAA GCC GCA CTC AGT (60)
TAT GGC TTC TAC GGC TGC TGC CAC TGT GGC GTG GGT GGC AGA GGA TCC CCC AAG GAT GCA ACG (120)
GAT CGC TGC TGT GTC ACT CAT GAC TGT TGC TAC AAA CGT CTG GAG AAA CGT GGA TGT GGC (180)
ACC AAA TTT CTG AGC TAC AAG TTT AGC AAC TCG AAG AGC AGA ATC ACC TGT GCA AAA CAG (240)
GAC TCC TGC AGA AGT CAA CTG TGT GAG TGT GAT AAG GCT GCC ACC TGT TTT GCT AGA (300)
AAC AAG AAG ACC TAC AAT AAA AAG TAC CAG TAC TAT TCC AAT AAA CAC TGC AGA GGG AGC (360)
ACC CCT CGT TGC TGA

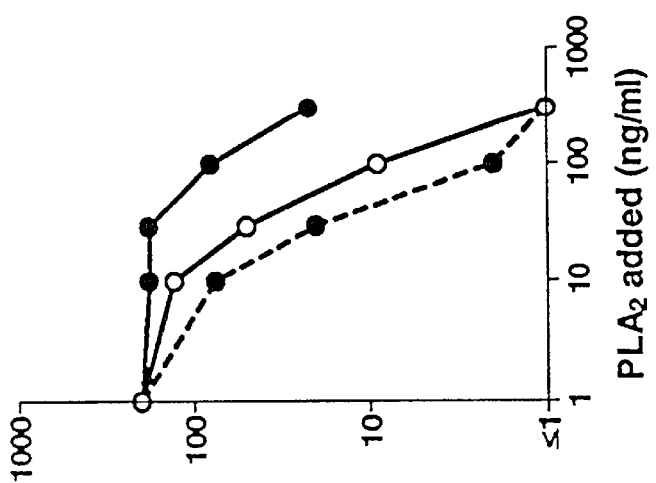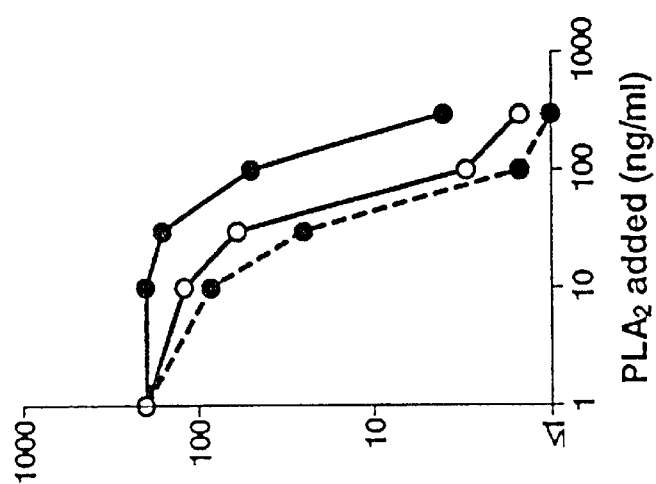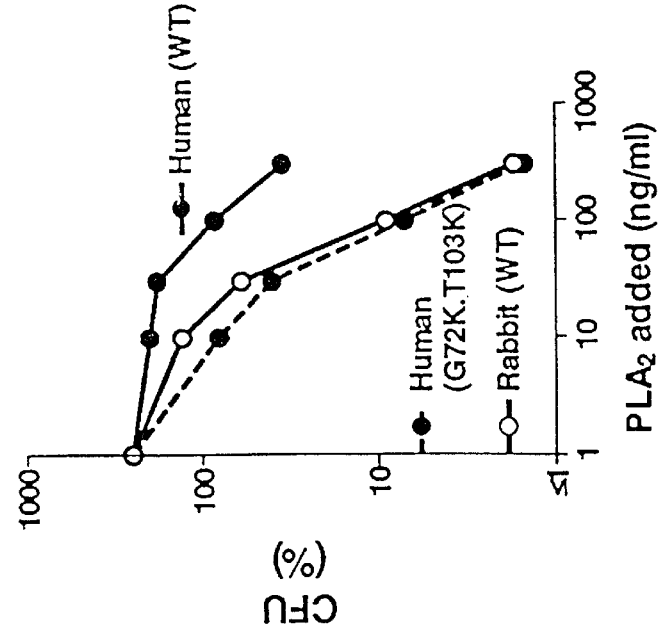

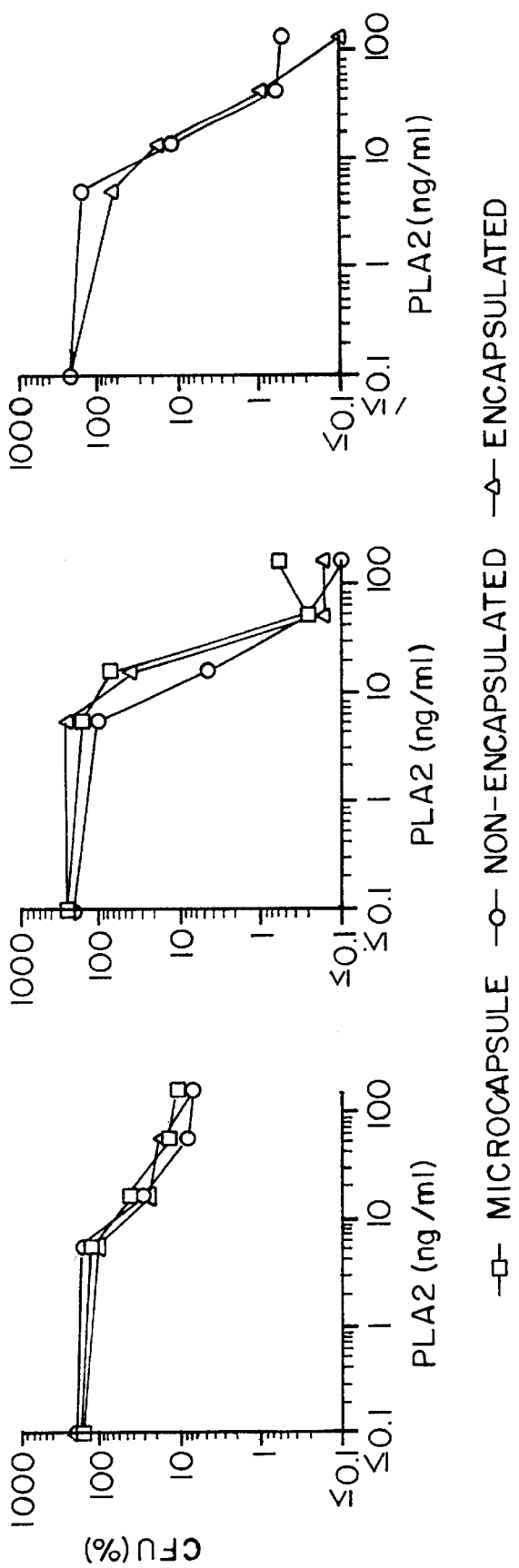

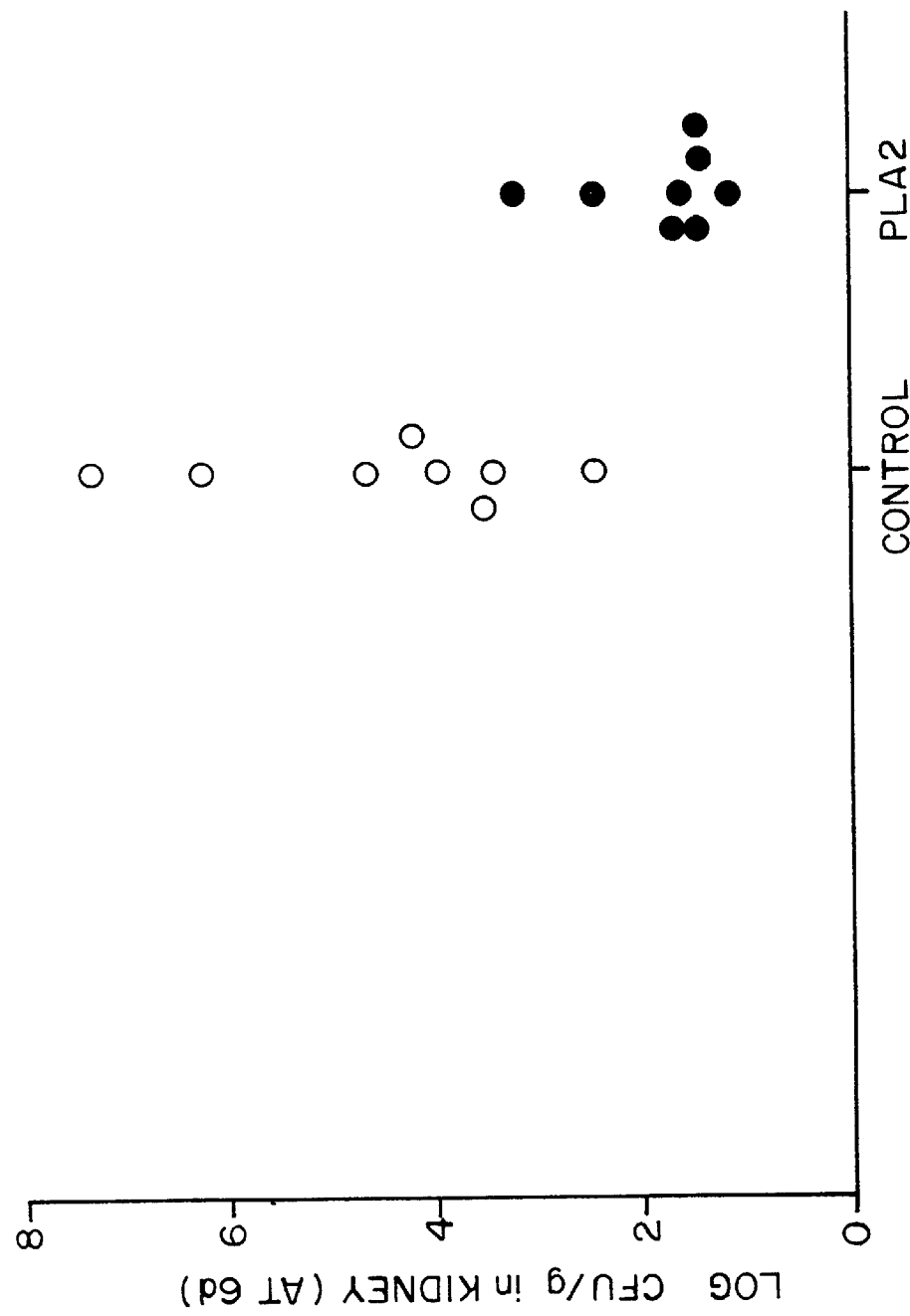

RECOMBINANT ANTIBACTERIAL GROUP IIA PHOSPHOLIPASE A2 AND METHODS OF USE THEREOF

The United States Government has certain rights to this invention by virtue of funding received from the U.S. Public Health Service Grant RO1-A1 18571.

This application claims priority under 35 U.S.C. §119 to provisional application No. 60/172,467 filed Dec. 17, 1999.

FIELD OF THE INVENTION

This invention pertains to a novel recombinant mutant protein of human Group IIA Phospholipase A2 (PLA2) which has significantly enhanced antibacterial activity compared to the wild-type human Group IIA PLA2, pharmaceutical formulations comprising the protein and methods of use thereof.

BACKGROUND OF THE INVENTION

The growing prevalence of antibiotic resistance in bacterial pathogens has stimulated renewed interest in the discovery of novel antibiotics. U.S. Pat. No. 5,874,079 discloses that a "Group IIA" 14 kDa Phospholipase A2 (PLA2), mobilized during inflammation expresses potent bactericidal activity toward a broad range of clinically important Gram-positive bacteria and enhances the activity of the host defense mechanisms toward many Gram-negative bacteria.

The phospholipase A2 (PLA2) family of enzymes hydrolyze the sn-2 ester of glycerophospholipids to produce a fatty acid and a lysophospholipid (Dennis, J.Biol. Chem. 269:13057–13060, 1994; Gelb et al, Ann. Rev. Biochem. 64, 653–688, 1995; Waite, The phospholipases, Plenum Press, New York, 1987). Based on amino acid sequences, 10 groups of PLA2s have been identified, including eight from mammals (Dennis, Trends Biochem. Sci. 22: 1–2, 1997; Cupillard et al., J. Biol. Chem. 272: 15745–15752, 1997). Group IIA PLA2 in mammals are produced by many different cell types including phagocytic cells, platelets, Paneth cells and lacrimal cells. It has been shown that both rabbit and human Group IIA PLA2 can, in concert with other host defense mechanisms, increase the destruction of gram-negative bacteria (Wright et al., J. Clin. Invest. 85: 1925–1935, 1990; Weiss et al., J. Biol. Chem. 269: 26331–26337, 1994 Elsbach et al., Trends Microbiol. 2: 324–328, 1994 and Madsen et al., Infect. Immun. 64: 2425–2430, 1996) and by itself, kill many gram-positive bacteria (Weinrauch et al., J. Clin. Invest. 97: 250–257, 1996). The antibacterial activity of Group IIA PLA2 appears to be a specific attribute of the mammalian 14 kDa isoform. This is further exemplified in experimentally induced local inflammatory (ascitic) fluid in rabbits, whereby the mobilization of Group IIA PLA2 is fully responsible for the potent bactericidal activity expressed in the fluid toward S. aureus and several other gram-positive bacteria (Weiss et al., en supra). Normal plasma, by contrast contains low levels of PLA2 and antistaphylococcal activity. It has recently been shown that the mobilization of this enzyme in baboons during inflammation may play an important role in host defense mechanisms against invading bacteria (Weinrauch et al., J. Clin. Invest. 102 (3): 633–638, 1998).

In biological fluids, as little as 100 ng/ml of the human Group II A PLA2 is sufficient to kill greater than 99% of $10^6$ Staphylcoccus aureus cells/ml, including all multi-drug resistant clinical isolates tested. The bactericidal activity of the PLA2 was dependent on catalytic activity and was enhanced synergistically by the co-treatment with sub-inhibitory doses of β-lactam antibiotics. The potent antibacterial activity of the mammalian Group IIA PLA2 is not expressed by other closely related PLA2s reflecting the presence and localization of a high density of basic residues in the Group IIA PLA2 that is absent in all other subsets of related PLA2s.

U.S. Pat. No. 5,874,079 discloses that the rabbit Group IIA PLA2 possesses 10 fold greater antibacterial activity than the human enzyme. Since it is preferable to treat humans with human-derived therapeutic proteins, what is needed is a human PLA2 with activity similar to the rabbit counterpart.

SUMMARY OF THE INVENTION

In one aspect, the present invention provides methods for treating Gram-positive bacterial infections in humans, by administering bactericidal-effective amounts of mutant human Group IIA PLA2.

In another aspect, the invention provides pharmaceutical formulations having bactericidal activity against Gram-positive bacteria. These formulations comprise bactericidal-effective concentrations of mutant human Group IIA PLA2 and a pharmaceutically acceptable carrier or diluent. Additionally, the formulations may comprise other bioactive compounds, such as, e.g., conventional antibiotics, that act additively or synergistically with Group IIA PLA2 to promote bacterial killing.

These and other aspects of the present invention will be apparent to those of ordinary skill in the art in light of the present description, claims and drawings.

BRIEF DESCRIPTION OF DRAWINGS

FIGS. 3(A and B) show the DNA (A), SEQ. ID. NO. 1 and the protein (B), SEQ. ID. NO. 2 sequence, respectively, of mutant human Group IIA PLA2. Residues differing from sequence of wild-type human Group IIA PLA2 are shown in bold and underlined.

FIG. 5 is a graphic illustration of the comparison of the bactericidal activity of human wild-type (WT), and mutant human and WT rabbit Group II A PLA2 towards S. aureus RN450 and two clinical isolates, strains 5A and 18 S. aureus.

FIGS. 6(A, B and C) are graphic illustrations showing WT human and WT rabbit and mutant human Group II A PLA2-induced killing of S. aureus strains expressing 1(A) 5(B) or 8(C) capsular serotype polysaccharides.

FIG. 11 is a graphical illustration showing that administration of the mutant human Group IIA PLA 2 reduces metastatic kidney infection caused by S. aureus.

DETAILED DESCRIPTION OF THE INVENTION

Figure 1A:
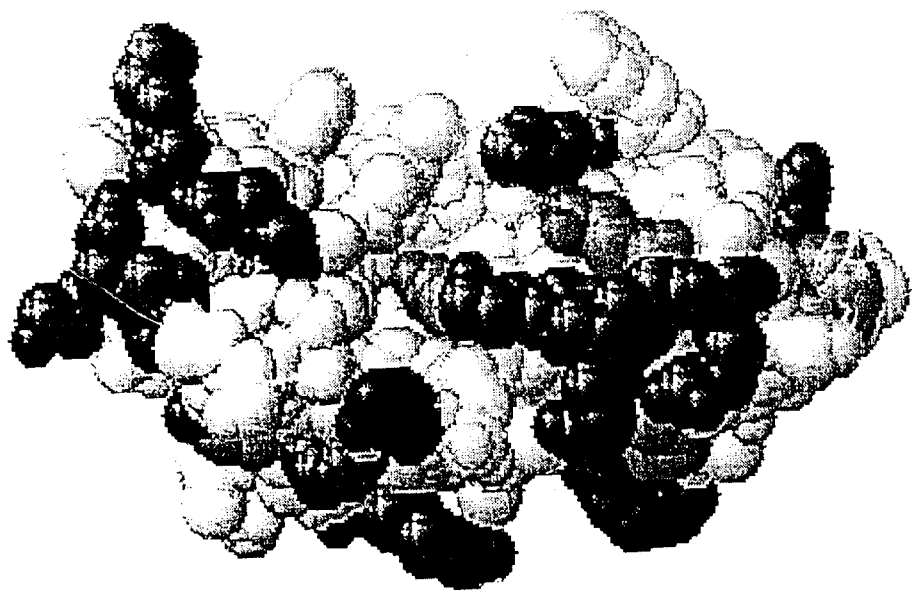
FIGS. 1(A, B, C and a,b,c) are space-filling models of wild-type human (FIGS. 1A, a), rabbit (FIGS. 1B, b) and mutant (G72K.T103K, FIGS. 1C, c) human Group IIA PLA2 showing the distribution of charged residues within these PLA2. Models are based on the solved X-ray structure of human Group IIA PLA2 (Scott, D. L., White, S. P., Browning, J. L., Rosa, J. J., Gelb, M. H., Sigler, P. B. 1991. Science 254: 1007–1010). Sites shown in black represent basic residues (arg and lys), sites in gray correspond to acidic residues (asp and glu). All other residues are displayed in white. Two images of each enzyme are shown corresponding to approximately 180 degree rotations (a, b, c), for WT human, WT rabbit and mutant human, respectively. Note that residues are numbered in a continuous fashion according to the primary structures of these PLA2s.
Figure 1A:
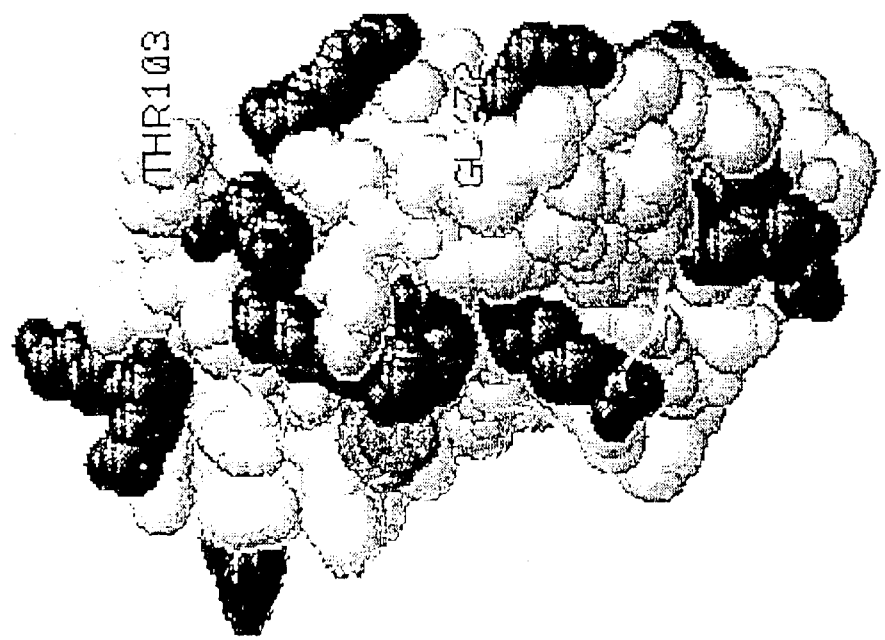
Figure 1B:
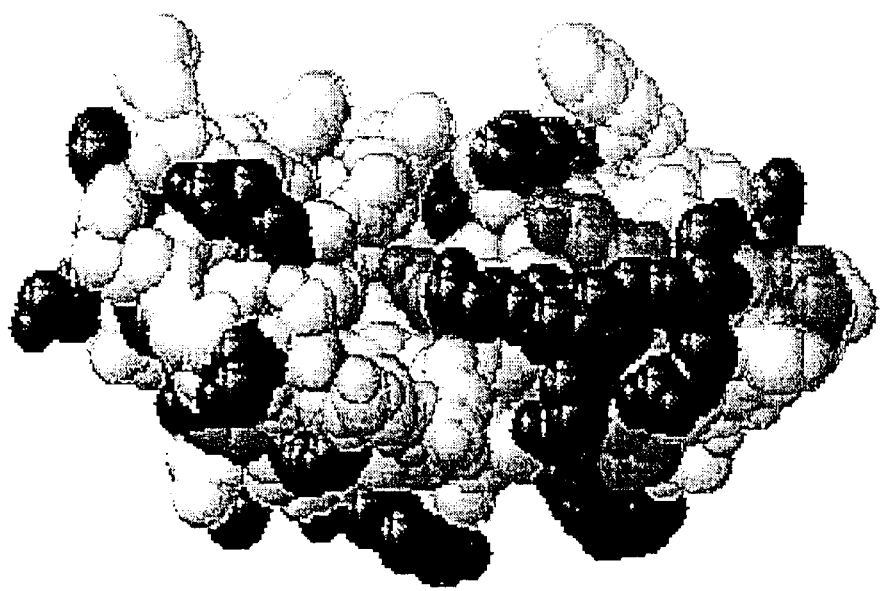
Figure 1B:
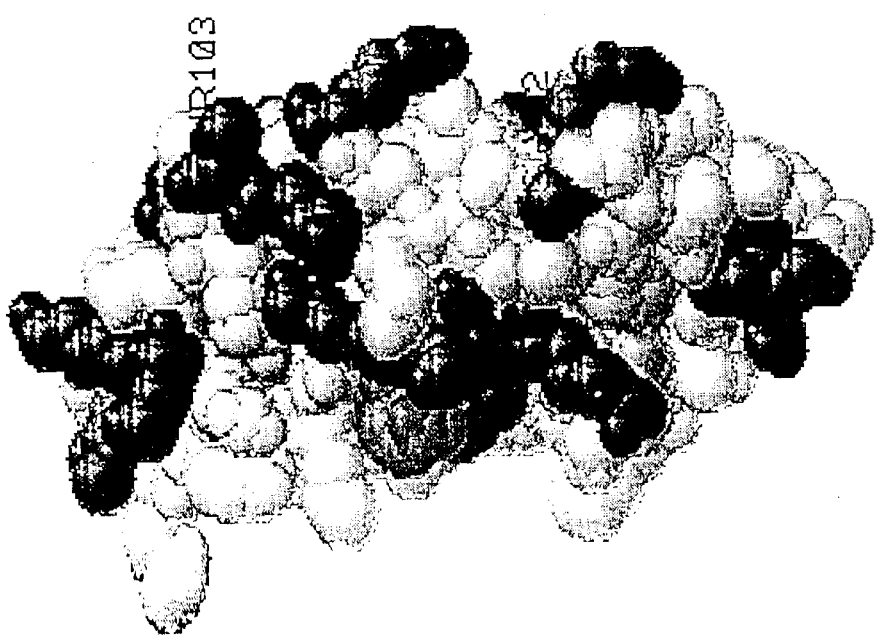

All patent applications, patents, and literature references cited in this specification are hereby incorporated by reference in their entirety.

Definitions

1. "Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases.

2. An "isolated" nucleic acid or polypeptide as used herein refers to a nucleic acid or polypeptide that is removed from its original environment (for example, its natural environment if it is naturally occurring). An isolated nucleic acid or polypeptide contains less than about 50%, preferably less than about 75%, and most preferably less than about 90%, of the cellular components with which it was originally associated.

3. A nucleic acid or polypeptide sequence that is "derived from" a designated sequence refers to a sequence that corresponds to a region of the designated sequence. For nucleic acid sequences, this encompasses sequences that are homologous or complementary to the sequence, as well as "sequence-conservative variants" and "function-conservative variants." For polypeptide sequences, this encompasses "function-conservative variants." Sequence-conservative variants are those in which a change of one or more nucleotides in a given codon position results in no alteration in the amino acid encoded at that position. Function-conservative variants are those in which a given amino acid residue in a polypeptide has been changed without altering the overall conformation and function of the native polypeptide, including, but not limited to, replacement of an amino acid with one having similar physicochemical properties (such as, for example, acidic, basic, hydrophobic, and the like). "Function-conservative" variants also include any polypeptides that have the ability to elicit antibodies specific to a designated polypeptide.

In general, nucleic acid manipulations used in practicing the present invention employ methods that are well known in the art, as disclosed in, e.g., *Molecular Cloning, A Laboratory Manual* (2nd Ed., Sambrook, Fritsch and Maniatis, Cold Spring Harbor) and *Current Protocols in Molecular Biology* (Eds. Ausubel, Brent, Kingston, More, Feidman, Smith and Stuhl, Greene Publ. Assoc., Wiley-Interscience, NY, N.Y., 1997).

The present invention is directed to methods and compositions for killing Gram-positive bacteria that take advantage of the bactericidal action of Group IIA phospholipase A2 (PLA2). In practicing the invention, bacteria are exposed to or contacted with, a Gram-positive bactericidal-effective amount of mutant human Group IIA PLA2, resulting in the rapid inactivation and death of Gram-positive bacteria. According to the invention, bacterial infections in humans can be treated by administering mutant human Group IIA PLA2. The invention also encompasses pharmaceutical formulations suitable for therapeutic administration.

The mutant human Group II A PLA2 of the present invention has 10× greater antibacterial activity and a net charge +2 greater than the human WT homologue (+17 vs. +15). Based on the comparison of the structural and functional properties of rabbit and human wild-type and mutant Group II A PLA2 (see FIG. 1), discrete alterations of human Group II A PLA2 by site-specific mutagenesis yielded novel human Group II A PLA2 proteins (herein referred to as "mutant") with markedly enhanced antibacterial activity which may be measured using any procedure well-known in the art, including that described in Example 3 below.

Previous studies with site-specific mutants of human Group IIA PLA2 indicated that the high net (+) charge of Group IIA PLA2 in addition to its catalytic properties were essential for the potent antibacterial properties of Group IIA PLA2. The high net (+) charge and antibacterial properties are unique attributes of this subset of PLA2. In addition, comparison of the structural and functional properties of native and recombinant rabbit and human Group IIA PLA2 demonstrated higher antibacterial activity in the rabbit PLA2 along with a higher net (+) charge (+17 for the rabbit enzyme, +15 for the human PLA2). Following cloning of the cDNA encoding rabbit Group IIA PLA2 and sequence analysis, comparison of the primary structures of rabbit and human Group IIA PLA2 revealed 32 sites that were different in these two enzymes (26% of 124 residues; no gaps). Of these, at least 22 represented relatively conservative substitutions. Two differences stood out; arginine (rabbit) vs. glycine (human) at residue 72 and lysine (rabbit) vs. threonine (human) at residue 103. These differences account for the higher net charge of the rabbit PLA2 and were located along a highly cationic ridge on the enzyme surface (see FIG. 1). Mutagenesis studies indicated that the charge properties of this region are essential for potent antibacterial activity and also suggested that the charge properties of other regions may not be equally important for antibacterial activity. Consequently, residues 72 and 103 were chosen for mutagenesis. It is possible that introduction of basic residues either at other surface sites within this highly cationic ridge or outside this region, even at sites that do not normally contain basic amino acids in the native Group IIA PLA2, could also confer increased antibacterial activity.

It should be noted that among all the "low Mr" (i.e. 13–18 kDa) PLA2, including the native Group IIA PLA2, the density and distribution of charged residues along the enzyme surface varies widely without affecting overall protein conformation and catalytic activity toward artificial substrates. This is also true in surface charge changes introduced genetically in PLA2 variants. Thus, great variation in the enzyme surface charge can be well tolerated, affording ample opportunity to create many permutations of enzyme structure that may enhance antibacterial potency.

Figures 3A, 3B:
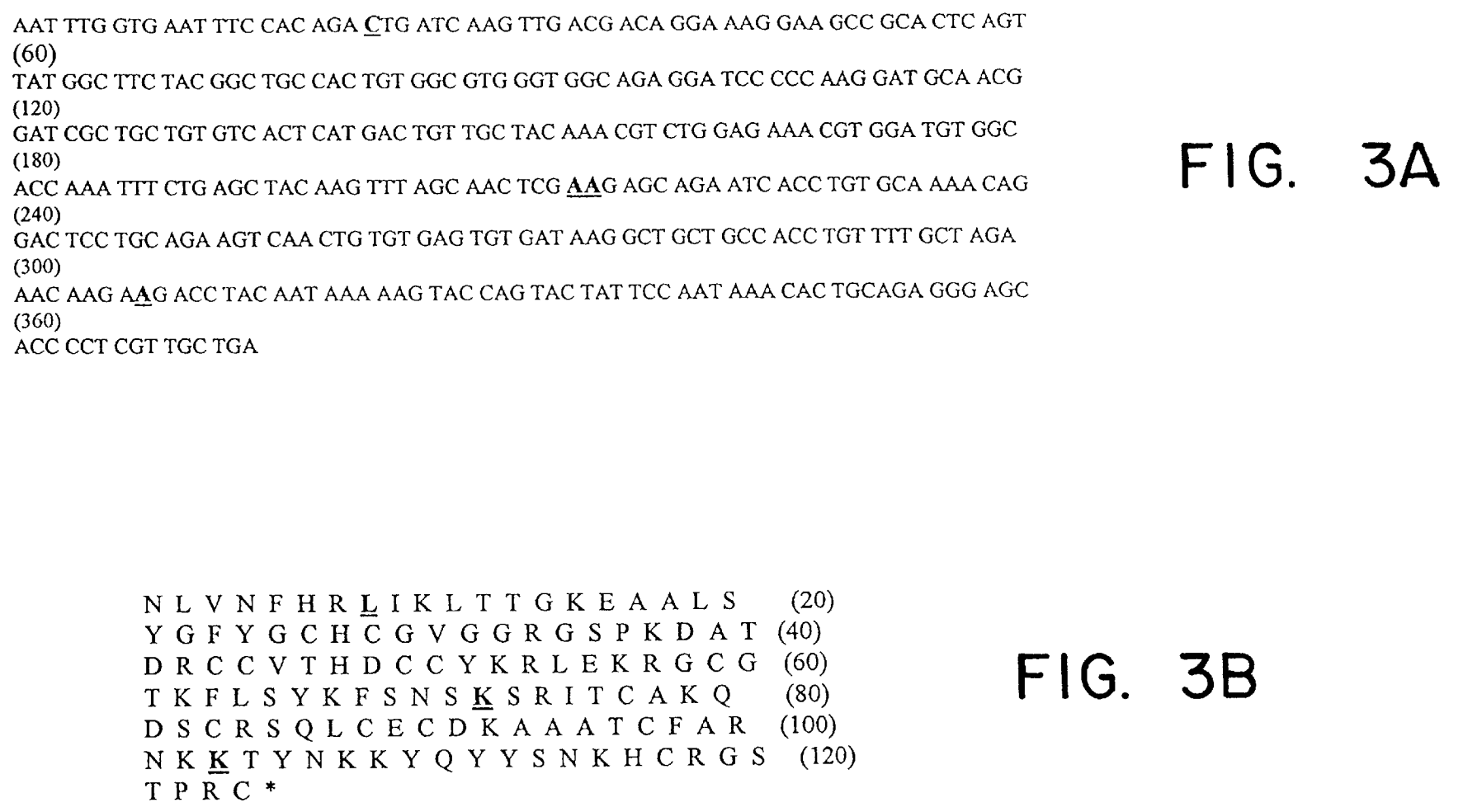

In a preferred embodiment, *E. coli* is stably transformed with a cDNA encoding mutant human Group IIA PLA2, as set forth in FIG. 3A and is used as a recombinant source of Group IIA PLA2 (see Example 1). For recombinant expression, Group IIA PLA2-encoding DNA, contained within a DNA vector, must be operably linked to a transcriptional promoter so that functional Group IIA PLA2 mRNA is transcribed and Group IIA PLA2 protein is synthesized within the transformed host cell. Preferably, the recombinant protein is recovered in *E. coli* inclusion bodies and then the expressed protein is subjected to in vitro reversible denaturation/reduction followed by renaturation/oxidation to promote proper disulfide bond formation.

The invention also encompasses vectors comprising mutant human PLA2-encoding sequences, cells comprising the vectors, and methods for producing mutant human PLA2 that involve culturing the cells.

A large number of vectors, including plasmid and fungal vectors, have been described for expression in a variety of eukaryotic and prokaryotic hosts. Advantageously, vectors may also include a promotor operably linked to the mutant human PLA2 encoding portion. The encoded mutant human PLA2 may be expressed by using any suitable vectors and host cells, using methods disclosed or cited herein or otherwise known to those skilled in the relevant art. The particular choice of vector/host is not critical to the invention.

Vectors will often include one or more replication systems for cloning or expression, one or more markers for selection in the host, e.g. antibiotic resistance, and one or more expression cassettes. Ligation of the coding sequences to the transcriptional regulatory sequences may be achieved by known methods. Suitable host cells may be transformed/transfected/infected by any suitable method including electroporation, $CaCl_2$ mediated DNA uptake, fungal infection, microinjection, microprojectile, or other established methods.

Appropriate host cells include bacteria, archebacteria, fungi, especially yeast, and plant and animal cells, especially mammalian cells. Of particular interest are *E. coli, B. subtilis, S. cerevisiae,* SF9 cells, C129 cells, 293 cells, Neurospora, CHO cells, COS cells, HeLa cells, and immortalized mammalian myeloid and lymphoid cell lines. Preferred replication systems include M13, ColE1, SV40, baculovirus, lambda; adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under the appropriate expression conditions, host cells can be used as a source of recombinantly produced mutant human PLA2.

Nucleic acids encoding mutant human PLA2 polypeptides may also be introduced into cells by recombination events. For example, such a sequence can be introduced into a cell, and thereby effect homologous recombination at the site of an endogenous gene or a sequence with substantial identity to the gene. Other recombination-based methods, such as non-homologous recombinations or deletion of endogenous genes by homologous recombination, may also be used.

The invention also encompasses isolated and purified mutant human PLA2 polypeptides, including, e.g., a polypeptide having the amino acid sequence depicted in FIG. 3B, as well as function-conservative variants of this polypeptide, including fragments that retain antibacterial activity as described above.

Purification of mutant human Group IIA PLA2 from recombinant sources may be achieved by methods well-known in the art, including without limitation ion-exchange chromatography, reversed-phase high performance liquid chromatography (HPLC) on C4 columns, gel filtration, isoelectric focusing, affinity chromatography, immunoaffinity chromatography, and the like. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix.

In a preferred embodiment, a cell-free fluid containing mutant human Group IIA PLA2 is subjected to ion-exchange chromatography on SP-Sepharose, followed by reversed-phase high performance liquid chromatography (HPLC) on a C4 column. Purity of the final Group IIA PLA2 preparations is confirmed by SDS-PAGE and by OD at 280 m, using the known extinction coefficient for this protein (OD of 1.0=0.9 mg/ml).

The isolated polypeptide may be modified by, for example, phosphorylation, sulfation, acylation, or other protein modifications. It may also be modified with a label capable of providing a detectable signal, either directly or indirectly, including, but not limited to, radioisotopes and fluorescent compounds.

According to the present invention, the mutant human Group IIA PLA2 of the present invention is characterized by bactericidal activity against gram positive bacteria, such as *S. aureus* (see Example 3). Antibacterial activity of mutant human Group IIA PLA2 may be quantified by measuring the colony-forming ability of susceptible bacteria that have been incubated with or without increasing amounts of mutant human Group IIA PLA2. Typically, a suspension of $10^6$ bacteria/ml (e.g., *S. aureus*) is exposed to 1–500 ng/ml of mutant human Group IIA PLA2 for 60–90 minutes at 37° C., after which the cells are mixed with molten agar and plated. After overnight growth, bacterial colonies are compared between mutant Group IIA PLA2-treated and untreated cultures.

The present invention encompasses, in addition to the mutant human Group IIA PLA2 disclosed herein, other recombinant forms of Group IIA PLA2 that are formed by site-specific genetic manipulations and have detectable Gram-positive bactericidal activity. The methods and compositions of the present invention encompass any deletion, addition, or substitution mutant of Group IIA PLA2 produced by the methods described herein that increase the wild-type enzymatic and antibacterial activity.

It will be understood that the methods for expression, purification, and activity measurements described above for the mutant human Group IIA PLA2 can also be applied to variant Group IIA PLA2 species. Thus also, only routine experimentation is required to identify additional, new useful Group IIA PLA2 variants.

Therapeutic Applications

The enhanced antibacterial potency of the mutant human Group II A PLA2 protein described herein provides new therapeutic approaches to the treatment of potentially life-threatening infections caused by multi-drug resistant Gram-positive bacteria. The applications include wound and bloodstream infections with methicillin-resistant *S. aureus*

(MRSA) and nosocomial infections with vancomycin-resistant *Enterococcus faecium*. These infections are much more common and potentially life threatening in immunocompromised or hospitalized patients. The ability of the Group II A PLA2 to act in synergy with various β-lactam antibiotics and, most importantly, with otherwise β-lactam-resistant bacteria (e.g. MRSA), also allows for the use of the PLA2 of the present invention in conjunction with antibiotics otherwise rendered ineffective by the growing prevalence of antibiotic resistance.

According to the present invention, recombinant mutant human Group IIA PLA2 may be formulated with a physiologically acceptable carrier, such as, for example, phosphate buffered saline or deionized water. The pharmaceutical formulation may also contain excipients, including preservatives and stabilizers, that are well-known in the art. The compounds can be formed into dosage units such as, for example, liquids, tablets, capsules, powders, suppositories, and may additionally include excipients that act as lubricant(s), plasticizer(s), colorant(s), absorption enhancer(s), bactericide(s), and the like. The dosage forms may contain mutant human Group IIA PLA2 at concentrations ranging between about 100 ng/ml and about 100 μg/ml. Solid dosage forms such as tablets and powders may contain the mutant human Group IIA PLA2 of the present invention at appropriate concentrations so that bactericidal effective amounts of mutant human Group IIA PLA2 (see below) can be delivered using conventional administration regimens. It will be understood that the pharmaceutical formulations of the present invention need not in themselves contain the entire amount of the agent that is effective in treating the disorder, as such effective amounts can be reached by administration of a plurality of doses of such pharmaceutical formulations.

Modes of administration of the mutant human Group IIA PLA2 of the present invention to achieve a therapeutic benefit include topical, oral and enteral, intravenous, intramuscular, subcutaneous, transdermal, transmucosal (including rectal and buccal), and by-inhalation routes. Generally, Group IIA PLA2 and specifically the mutant human Group IIA PLA2 of the present invention are extremely stable proteins and tolerate a wide variety of environmental conditions. It will be understood that the mode of administration will depend on the nature of the syndrome, including the location. and severity of the Gram-positive bacterial infection. For example, skin lesions may be treated using a topical ointment, whereas a bacteremia may require intravenous administration. An internal but localized infection may be treated by injecting the formulation directly into the site of the infection.

An "effective amount" of the mutant human Group IIA PLA2 of the present invention for treating a particular bacterial infection is an amount that results in a detectable reduction in the severity of the infection. This may be measured directly, i.e., by counting or culturing the pathogenic microorganisms, or indirectly, by monitoring clinical signs of infection, such as fever or purulent discharge. Typically, administration of the mutant human Group IIA PLA2 will result in the lessening or amelioration of at least one symptom of the infection. Any amelioration resulting from administration of the mutant human Group IIA PLA2 of the present invention of any symptom of infection is within the scope of the invention. The effective amount for treating a given syndrome in a human can be determined by routine experimentation well-known in the art, such as by establishing a matrix of dosages and frequencies and comparing a group of experimental units or subjects to each point in the matrix.

An additional consideration in establishing the optimum dosage of the mutant human Group IIA PLA2 for treating bacterial infections is potential toxicity. Though there have been reports that Group IIA PLA2 possesses inflammatory activity (see, for example, Bomalaski et al., *J Immunol.* 146:3904, 1991; and Cirino et al., *J Rheumatol.* 21:824, 1994), this phenomenon was only observed at Group IIA PLA2 concentrations several orders of magnitude higher than those at which bactericidal effects are observed. Furthermore, the preparations used in the studies cited above were contaminated with endotoxin, which itself has a potent inflammatory activity. Thus, without wishing to be bound by theory, it is believed that bactericidal effective amounts of Group IIA PLA2 can be administered to humans without causing inflammatory or other detrimental side effects. In addition, it is preferable to treat humans with Group IIA PLA2 derived from the same species.

The effective amount of the mutant human Group IIA PLA2 of the present invention for treating infections caused by gram-positive bacteria to be administered may range between about 1 and about 100 μg/kg/body weight, preferably from about 1 to about 10 μg/kg/body weight. In a preferred embodiment, mutant human Group IIA PLA2 of the present invention is formulated in a sterile saline solution, which is administered intravenously to a patient suffering from an antibiotic-resistant *S. aureus* bacteremia.

In another embodiment, an antibacterial formulation is prepared containing, in addition to the mutant human Group IIA PLA2, other conventional antibiotics (such as, for example, β-lactam antibiotics), or other bioactive substances, that may act additively or synergistically with the mutant human Group IIA PLA2 of the present invention to kill Gram-positive bacteria. It is believed that the use of formulations containing the mutant human Group IIA PLA2 of the present invention in conjunction with, for example, sub-lethal doses of other antibiotics would provide a clinical advantage in reducing the overall administration of antibiotics (thus lessening the development of antibiotic-resistant strains).

Antibiotics that can be used in conjunction with mutant human Group IIA PLA2 of the present invention in the methods and compositions of the present invention include without limitation penicillins (such as ampicillin, amoxicillin, oxacillin, and the like), cephalosporins, aminoglycosides (such as streptomycin, neomycin, kancmycin, gentamicin, and the like), tetracyclines, chloramphenical, and vancomycin. Commercial sources for each of these are presented in Table I below.

TABLE 1

| Drug | Source | City, State |
|---|---|---|
| Ampicillin | Warner Chilcott Laboratories | Rockaway, NJ |
| Amoxicillin | Warner Chilcott Laboratories | Rockaway, NJ |
| Oxacillin | Teva Pharmaceuticals | Sellersville, PA |
| Cefotaxime | Hoechst Marion Roussel | Kansas City, MO |
| Streptomycin | Pfizer | New York, NY |
| Neomycin | Merck | West Point, PA |
| Kanamycin | SolePak Pharmaceuticals | Boca Raton, FL |
| Gentamicin | SoloPak Pharmaceuticals | Boca Raton, FL |
| Tetracycline | Lederle Standard Products | Philadelphia, PA |
| Chloramphenicol | Fujisawa | Deerfield, IL |
| Vancomycin | Eli Lilly and Co. | Indianapolis, IN |

As shown below in Example 7, the human mutant Group IIA PLA2 of the present invention was effective in treating *S. aureus* infection in vivo. Given the rapidly spreading occurrence of drug resistant bacteria, the mutant enzyme of the present invention will provide a useful addition to the arsenal of presently used anti-Gram positive antibiotics.

The following examples are intended to further illustrate the invention without limiting the scope thereof.

EXAMPLE 1
Preparation of Mutant (G72K.T103K) Human Group II A PLA2 cDNA cDNA encoding the mutant human Group II A phospholipase A2 was produced by mismatched primer PCR using oligonucleotide primers directed against wild-type human Group II PLA 2 cDNA (clone hp PLA2 9-1) subcloned within pEE14 (CellTech) as described in Weiss, et al., 1994, J. Biol. Chem. 269: 26331–26337. The oligonucleotide primer 5' TTTGCTAGAAACAAGAAGACCTACAAT 3' SEQ. ID NO:3 has a single base pair change (underlined and in bold) conferring the threonine to lysine substitution at residue 103 and is complementary to codons 98–106 of the non-coding strand of the human Group II A phospholipase A2. The single mutant T103K was created by substitution of lysine for threonine at residue 103. The double mutant G72K.T103K was constructed on the DNA template of the T103K mutant using the primer 5' TTTAGCAACTCGAAGAGCAGAATCACC 3' SEQ. ID NO:4 which is complementary to the non-coding strand from residues 68–76 with the indicated two base change to produce the glycine to lysine substitution at residue 72. Furthermore, to facilitate purification of recombinant Group II A PLA2, expressed as part of a fusion protein, one additional substitution was introduced (L8M) using the oligonucleotide primer 5' GCTCGAGATGAATTTGGTGAATTTCCACAGACTGATC 3' SEQ. ID NO:5 which is complementary to the non-coding strand of the human Group II A PLA2 from codons 1–9. This alteration eliminates the single methionine amino acid residue within the PLA2 coding region permitting excision of intact PLA2 from the fusion partner by CNBr treatment.

EXAMPLE 2
Expression and Purification of Mutant (G72K.T103K) Human Group IIA PLA2

The mutated Group II A PLA2 cDNA was subcloned into Xho I and EcoRI restriction sites of *E. coli* expression vector pRSETA (Invitrogen) and expressed as a fusion protein under the control of the bacteriophage T7 promoter. Expression of the recombinant protein was induced by the treatment of transformed *E. coli* BL21 (DE3) with IPTG. The recombinant protein was recovered in inclusion bodies, extracted and modified by S-sulfonation as previously described. (Thannhauser et al., Biochemistry 24 7681–7688., 1985; Liang, N. S. et al. FEBS Letters 334:55–59. 1993; Fourcade et al., Cell 80: 919–923, 1995). The S-sulphonated protein was precipitated by dialysis against 1% acetic acid and cleaved by cyanogen bromide to release mature Group IIA PLA2 from the fusion protein. Refolding and disulfide bond formation of recombinant Group IIA PLA2 was carried out in the cold for 72 hours in 10 mM sodium borate buffer (pH 8.5) containing 2 mM cystine, 10 mM cysteine, 10 mM $CaCl_2$ and 0.85 M guanidinium hydrochloride followed by dialysis against 50 mM sodium acetate/acetic acid buffer, pH 5.0. Refolded, active Group IIA PLA2 was purified from improperly folded, inactive protein by chromatography on SP-Sepharose and reversed-phase high performance liquid chromatography (HPLC) on a C4 column. The purity of the recovered Group IIA PLA2 was confirmed by analytical reversed-phase HPLC and by absorbence at 280 nm, using the known extinction coefficient for this protein (OD of 1.0=0.9 mg/ml).

EXAMPLE 3
Comparison of the Bactericidal Activity of Wild-type and Recombinant Human, and Rabbit Group IIA PLA2s Against *Staphylococcus aureus* 52A The bactericidal activity of wild-type human and recombinant mutant human and rabbit Group IIA PLA2s against *Staphylococcus aureus* 52A ($10^6$ per ml) was determined. *S. aureus* was incubated with 0.01–100 nM of each Group IIA PLA2 and incubated at 37° C. for 2 hours in RPMI-1640 medium containing 10 mM HEPES, pH 7.4 and 1% (w/v) albumin. After incubation, bacterial viability was determined by measuring the colony forming ability of the bacteria in trypticase soy agar. Bacterial colonies were enumerated after 18–24 hours at 37° C. The results are expressed as the percentage of the colony forming units (CFU) of the original bacterial inoculum (i.e. at T=0).

Figure 2:
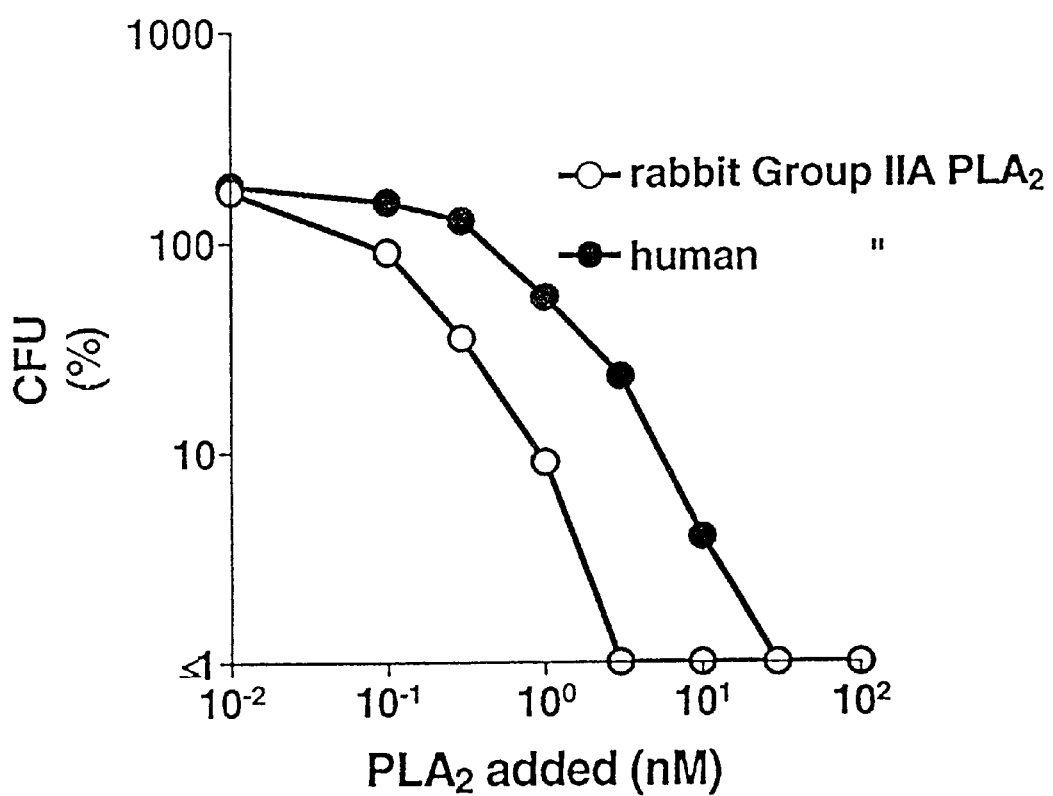
FIG. 2 is a graphic illustration of the comparison of bactericidal activity of native human and rabbit Group II A PLA2 towards S. aureus 52A.

The graphical results depicted in FIG. 2 show that about 10-fold lower concentrations of rabbit PLA2 than of human PLA2 suffice to produce the same reduction of CFU. Therefore, rabbit Group IIA PLA2 had a greater bactericidal effect on *S. aureus* cells than the human enzyme.

EXAMPLE 4
Comparison of the Bactericidal Activity of Wild-type (WT) and Recombinant Human, and Rabbit Group II A PLA2 Toward *S. aureus* RN450

The bactericidal activity of wild-type and recombinant mutant human and rabbit Group IIA PLA2s against *Staphylococcus aureus* RN450 was determined.

*S. aureus* RN450 ($10^6$/ml) was incubated with 1–500 ng/ml of each Group IIA PLA2 at 37° C. for 60 minutes in RPMI-1640 medium containing 10 mM HEPES, pH 7.4 and 1% (w/v) albumin. Bacterial viability was determined as in Example 3.

Figure 4:
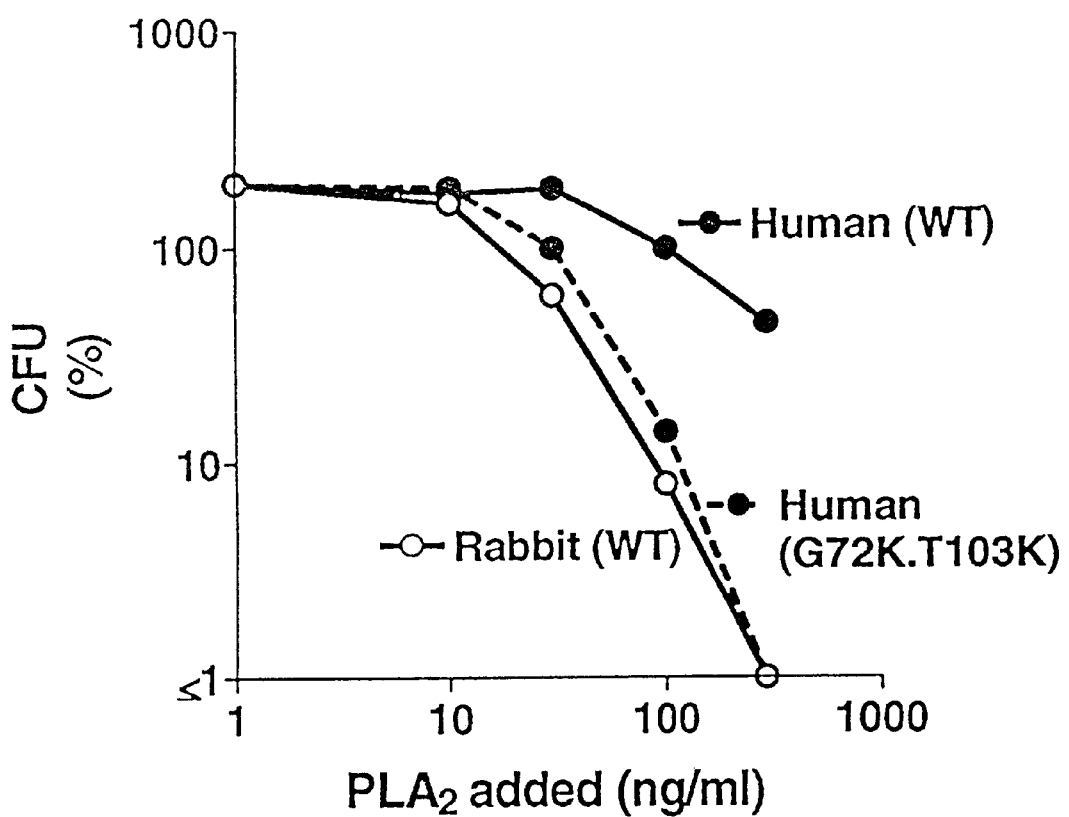
FIG. 4 is a graphic illustration of the comparison of the bactericidal activity of human wild-type (WT) and mutant human and WT rabbit Group II A PLA2 toward S. aureus RN450.

The graphical results depicted in FIG. 4 show that the bactericidal activities of recombinant mutant human Group IIA PLA2 and WT rabbit Group IIA PLA2 are nearly equivalent. Furthermore, the genetically modified mutant human Group IIA PLA2 had increased antibacterial activity against *S. aureus* compared to wild-type human Group IIA PLA2.

EXAMPLE 5
Comparison of the Bactericidal Activity of Recombinant Human and Rabbit Group II A PLA2 Toward *S. aureus* RN450 and Two Clinical Isolates, Strains 5A and 18

*S. aureus* RN450 and two clinical isolates, strains 5A (MRSA) and 18 ($10^7$/ml were incubated with 1–500 ng/ml of each Group IIA PLA2 at 37° C. for 90 minutes in 70% (v/v) pooled human sera diluted in Hanks' balanced salts solution and buffered with 10 mM HEPES, pH 7.4.

As shown in FIGS. 4 and 5, the mutant human Group IIA PLA2 was essentially as active as the wild-type rabbit enzyme toward each of the several strains of *S. aureus*, and, hence, significantly more active than the wild-type human Group IIA PLA2. This is manifested in both an artificial laboratory medium (FIG. 4) and in an environment that more closely simulates that of circulating body fluids (FIG. 5).

These findings further demonstrate that the novel mutant Group IIA phospholipase A2 described herein represents a more potent antibacterial product than the wild-type human enzyme.

EXAMPLE 6

Encapsulated and Non-encapsulated *S. aureus* are Killed by Group IIA PLA2

Figure 7A:
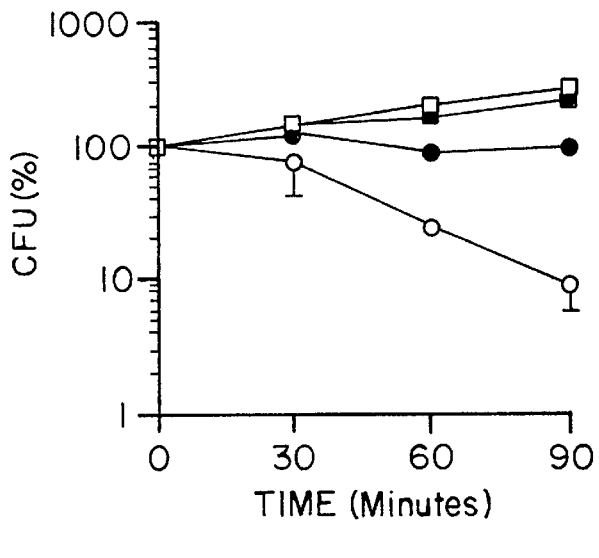
FIGS. 7(A and B) is a graphic illustration showing that encapsulated (A) and non-encapsulated (B) S. aureus were equally susceptible to killing by a whole inflammatory fluid and that killing of both strains was prevented by neutralizing antiserum to Group IIA PLA 2.
Figure 7B:
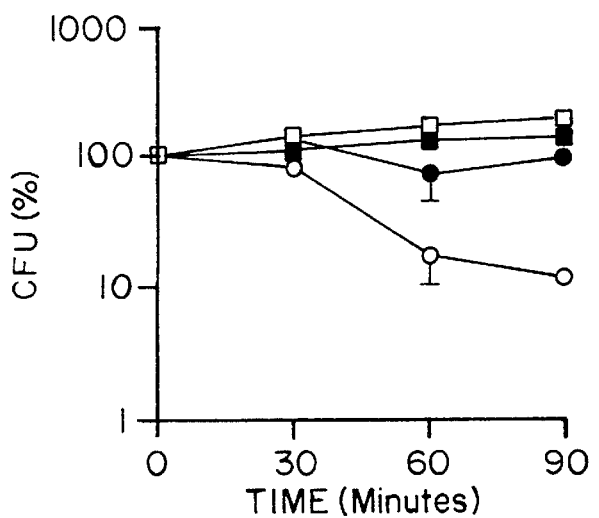
Figure 8:
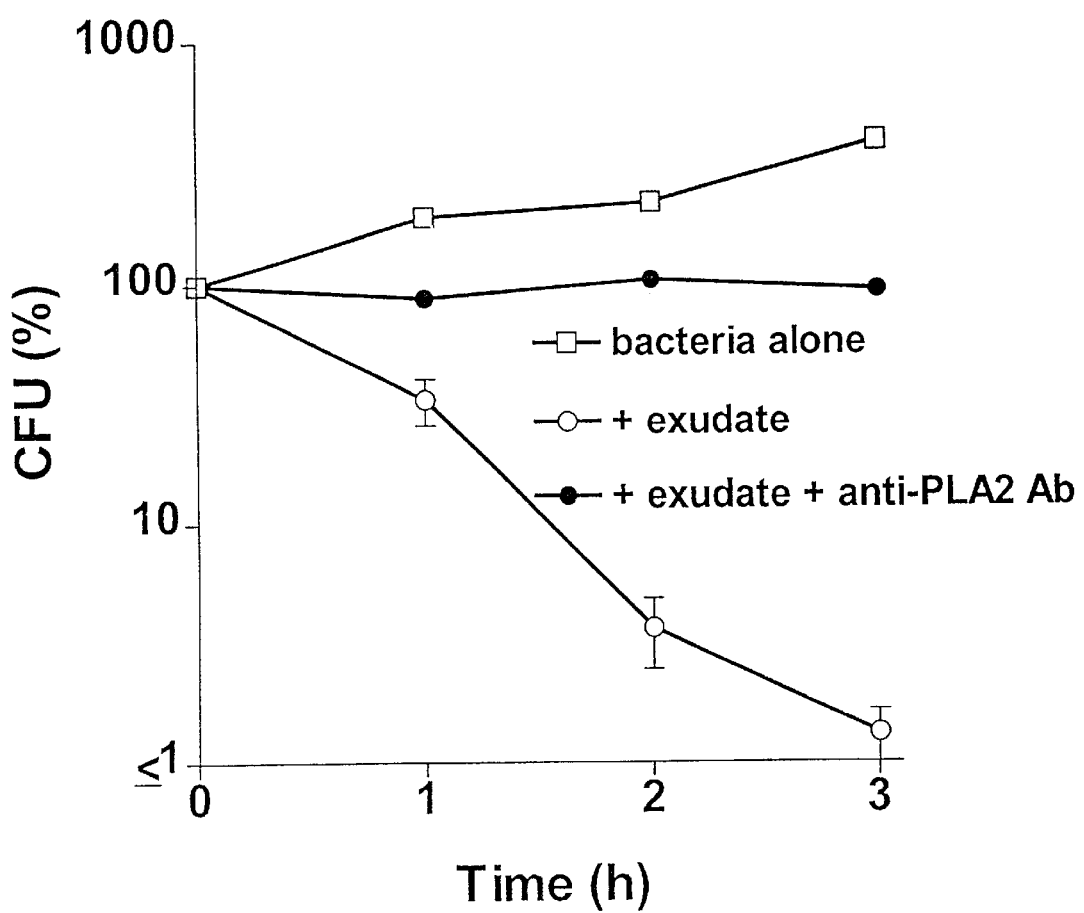
FIG. 8 is a graphic illustration showing that the killing of encapsulated S. aureus by whole inflammatory exudates is blocked by Group IIA PLA2 antiserum.

One setting in which mobilization of extracellular Group IIA PLA2 may be particularly important is against encapsulated strains of *S. aureus*. The majority of bacteremic isolates of *S. aureus* are encapsulated (Hochkeppel et al., *J. Clin. Microbiol.* 25:526–530) and bacteria recovered from more chronically infected sites as in cystic fibrosis are also covered with an extracellular carbohydrate polymer (McKenney et al., *Science* 284:1523–1527). In the absence of type-specific anti-capsular antibodies, encapsulated strains are relatively resistant to opsonophagocytic killing by PMN (Xu et al., *Infect. Immun.* 60:1358–1362; Table I). In contrast, purified Group IIA PLA2 and PLA2 present in elicited inflammatory fluids exhibit equipotent bactericidal activity against encapsulated *S. aureus* and isogenic non-encapsulated derivates (FIGS. 6, 7). Moreover, despite inability of PMN within experimentally elicited acute inflammatory exudates to efficiently ingest encapsulated *S. aureus* (Table 2), the bacteria are still efficiently killed by the inflammatory exudates in an extracellular and PLA2-dependent fashion (FIG. 8). Thus, Group IIA PLA2 can provide a potent extracellular weapon against phagocytosis-resistant encapsulated bacteria that is fully active in inflammatory exudates.

TABLE 2

EFFECT OF CAPSULE ON SUSCEPTIBILITY OF
*S. AUREUS* TO PHAGOCYTOSIS BY RABBIT PMN

| Strain | Bacteria/100 PMN |
|---|---|
| 1B (non-encapsulated) | 43.5 |
| 1C (encapsulated) | 2.3 |

*S. aureus* type 1C (encapsulated) and an isogenic non-encapsulated derivative (type 1B) were incubated for 30 min. with rabbit pentaneal exudate PMN at bacteria/PMN ratio of 2:5 ($10^6$ bacteria and $2.5 \times 10^6$ PMN/ml). At end of incubation, suspensions were diluted, smears prepared by cytospin and stained. PMN-associated bacteria were visualized by light microscopy and counted. Results are expressed as number of bacteria associated with PMN/100 PMN counted. Results indicate a 100% uptake of non-encapsulated bacteria and <10% uptake of encapsulated bacteria. Similar results were obtained when incubations were carried out in HEPES-bufferred Hanks' balanced salt solution or in $PLA_2$-depleted ascitic fluid.

EXAMPLE 7

Animal Experiment to Test Efficacy of Administered Human Mutant Group IIA PLA2 Against *S. aureus* Infection in vivo Materials and Methods In the example presented below, the following materials and methods were used.

Animals: CD/1 mice

Bacteria: Reynolds strain of *Staphylococcus aureus* (encapsulated; grown overnight on Columbia agar to maximize encapsulation as in experiments shown in Example 6).

Administration of bacteria: $2 \times 10^7$/ml in 0.2 ml of sterile RPMI supplemented with 10 mM HEPES (pH 7.4) and 1% bovine serum albumin. Intraperitoneal (i.p.) inoculation.

Adminstration of PLA2: 15 μg/0.2 ml of above medium i.p. approx. 10–15 min after inoculation of bacteria. Control animals received medium alone. Enzyme administered was Mutant [G72K.T103K] Group IIA PLA 2.

Assays of course of infection:

a) @ 30, 60, 120, and 240 min after infection, blood samples taken from tail vein from each of 4 animals in control and PLA2-treated groups. There were a total of 16 animals in each group; each animal was bled only once in this time period. Levels of bacteremia were assessed by measurement of bacterial CFU in blood.

b) @ 1 day after infection, 8 animals from each group were sacrificed. Blood was collected again to measure bacteremia and the peritoneal cavity was washed and inspected to look macroscopically for abscesses (none seen) and measure intraperitoneal bacteria by assay of CFU.

c) @ 6 days after infection, the remaining 8 animals from each group were sacrificed and infection in blood and peritoneal cavity was measured as above (still no abscesses seen). This animal model produces local and disseminated infection in control animals that is eventually self-limiting. The level of metastatic infection is greatest at approx. 6 days. In addition, kidneys were excised, weighed (no significant difference between animals within and between treatment groups) and homogenized to facilitate assay of bacterial CFU within infected kidney (i.e. representing metastatic infection). Abscesses were seen in two of 16 control animals; none were seen in PLA2-treated animals.

Figure 9:
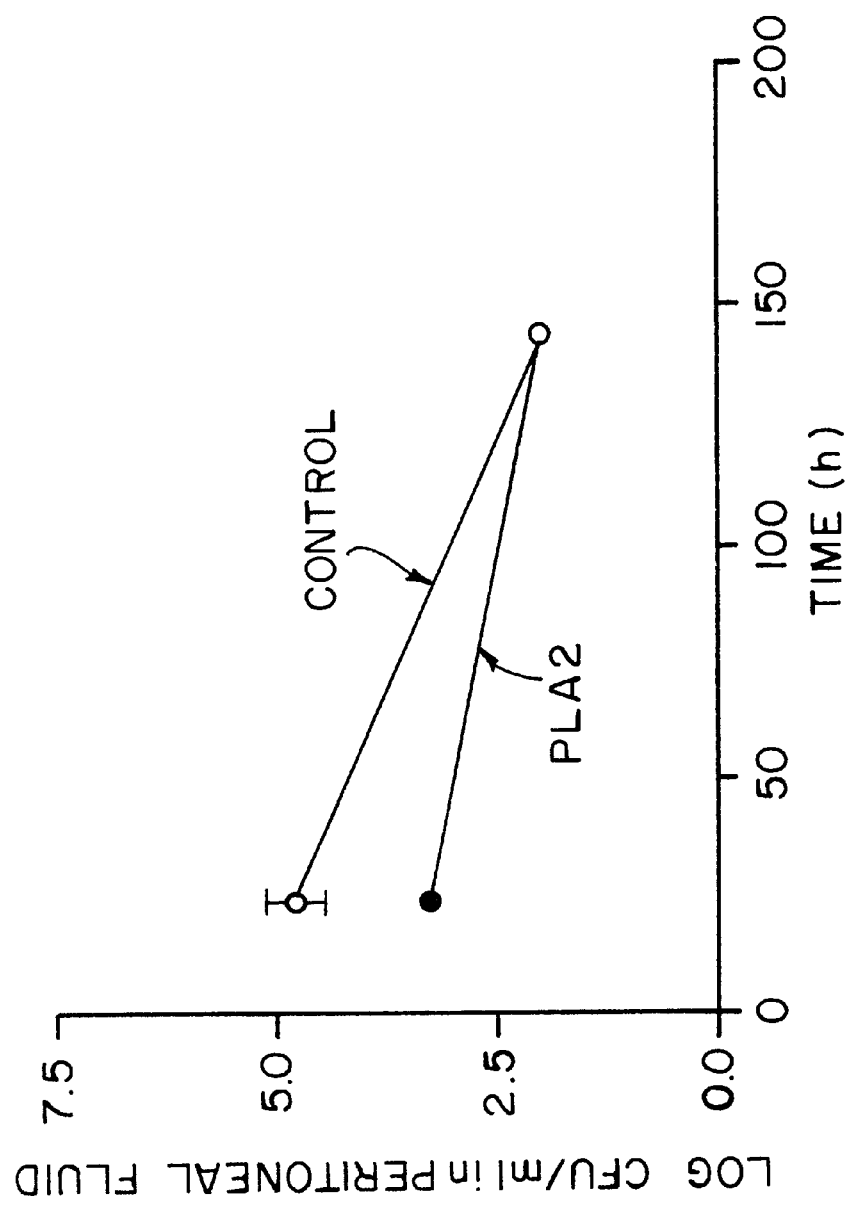
FIG. 9 is a graphical illustration showing that the mutant human Group IIA PLA 2 enzyme accelerates clearance of S. aureus infection in vivo.
Figure 10:
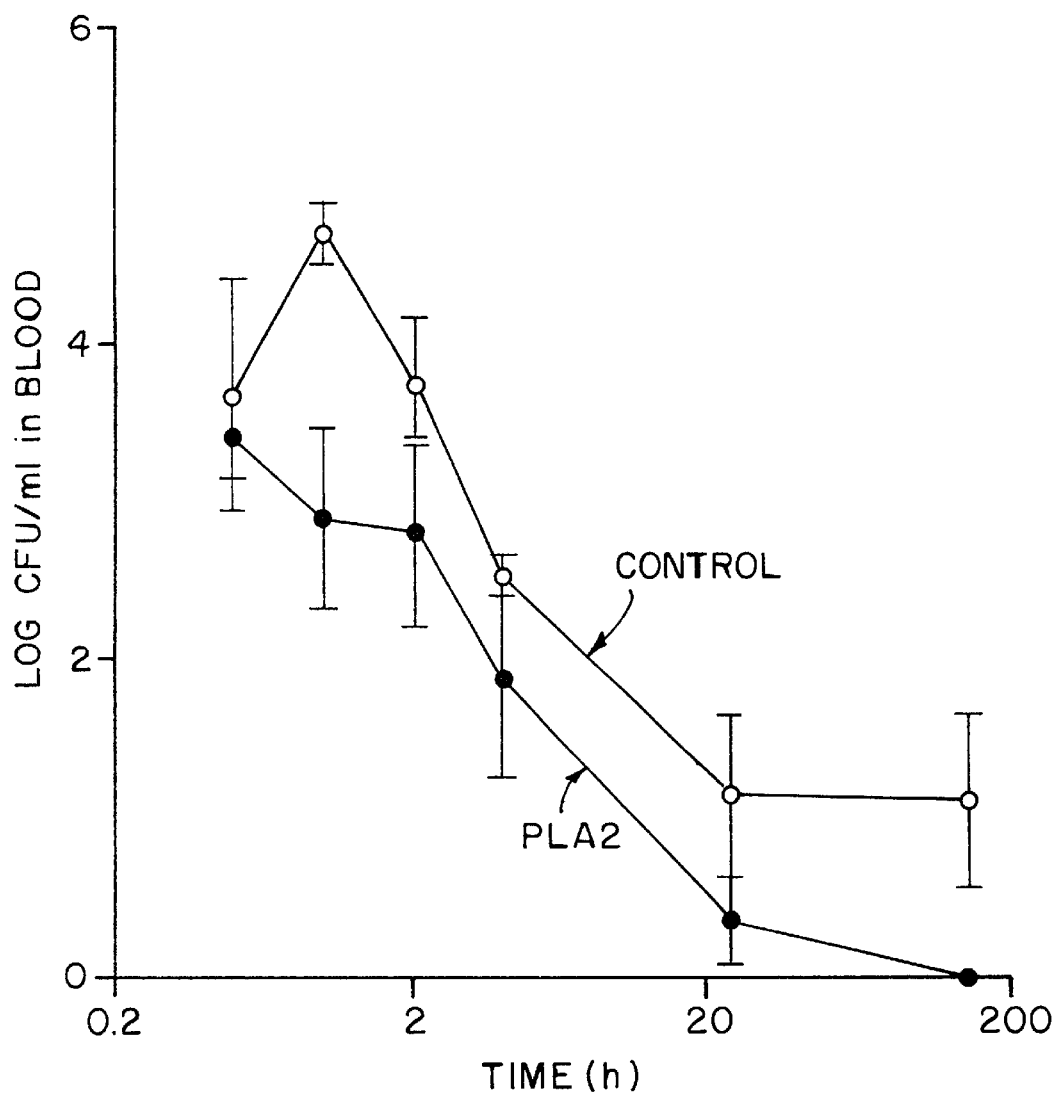
FIG. 10 is a graphical illustration showing that the mutant human Group II A PLA 2 reduces S. aureus bacteremia.

The results are shown in FIGS. 9, 10 and 11 for b, a and c, respectively, above.

---

What is claimed is:

1. A method for killing Gram-positive bacteria in a human patient which comprises contacting said bacteria with a bactericidal-effective amount of mutant human Group IIA phospholipase A2 (Group IIA PLA2) having SEQ ID NO:2.

2. The method of claim 1, wherein said bacteria are selected from the group consisting of Micrococcus, Staphylococcus, Streptococcus, Peptococcus, Peptostreptococcus, Enterococcus, Methanobacterium, Bacillus, Clostridium, Lactobacillus, Listeria, Erysipelothrix, Corynebacterium, Propionibacterium, Eubacterium, Actinomyces, Arachnia, Bifidobacterium, Bacterionema, Rothia, Mycobacterium, Nocardia, Streptomyces, and Micropolyspora.

3. The method of claim 1, wherein said bacteria are contacted with between about 1 and about 100 µg per kg body weight of said human patient of mutant human Group IIA PLA2.

4. The method for killing *Staphylococcus aureus* bacteria which comprises contacting said bacteria with a bactericidal-effective amount of mutant Group IIA PLA2 having SEQ ID NO:2.

5. A method for treating a *Staphylococcus aureus* infections in a human which comprises administering to said human an amount effective for treating said infection with mutant human Group IIA PLA2 having SEQ ID NO:2.

6. The method of claim 5 wherein said amount effective for treating said infection ranges between about 1 and about 100 µg/kg body weight of said human.

7. A method for treating a human patient suffering from an infection caused by a Gram-positive bacteria comprising administering to a human in need of such treatment:

(a) mutant human Group IIA PLA2 having SEQ ID NO:2, and (b) an antibiotic, the amounts of (a) and (b) together being effective to treat said infection.

8. The method of claim 7, wherein said antibiotic is selected from the group consisting of ampicillin, amoxicillin, oxacillin, cephalosporins, streptomycin, neomycin, kancmycin, gentamicin, tetracyclines, chloramphenical, and vancomycin.

* * * * *

SEQUENCE LISTING

<160> NUMBER OF SEQ ID NOS: 5

<210> SEQ ID NO 1
<211> LENGTH: 375
<212> TYPE: DNA
<213> ORGANISM: Homo sapiens

<400> SEQUENCE: 1

```
aatttggtga atttccacag actgatcaag ttgacgacag gaaaggaagc cgcactcagt      60
tatggcttct acggctgcca ctgtggcgtg ggtggcagag gatcccccaa ggatgcaacg     120
```

```
gatcgctgct gtgtcactca tgactgttgc tacaaacgtc tggagaaacg tggatgtggc      180
accaaatttc tgagctacaa gtttagcaac tcgaagagca gaatcacctg tgcaaaacag      240
gactcctgca gaagtcaact gtgtgagtgt gataaggctg ctgccacctg ttttgctaga      300
aacaagaaga cctacaataa aaagtaccag tactattcca ataaacactg cagagggagc      360
acccctcgtt gctga                                                       375
```

<210> SEQ ID NO 2
<211> LENGTH: 124
<212> TYPE: PRT
<213> ORGANISM: Homo sapiens
<400> SEQUENCE: 2

```
Asn Leu Val Asn Phe His Arg Leu Ile Lys Leu Thr Thr Gly Lys Glu
1               5                   10                  15

Ala Ala Leu Ser Tyr Gly Phe Tyr Gly Cys His Cys Gly Val Gly Gly
            20                  25                  30

Arg Gly Ser Pro Lys Asp Ala Thr Asp Arg Cys Cys Val Thr His Asp
        35                  40                  45

Cys Cys Tyr Lys Arg Leu Glu Lys Arg Gly Cys Gly Thr Lys Phe Leu
    50                  55                  60

Ser Tyr Lys Phe Ser Asn Ser Lys Ser Arg Ile Thr Cys Ala Lys Gln
65                  70                  75                  80

Asp Ser Cys Arg Ser Gln Leu Cys Glu Cys Asp Lys Ala Ala Ala Thr
                85                  90                  95

Cys Phe Ala Arg Asn Lys Lys Thr Tyr Asn Lys Lys Tyr Gln Tyr Tyr
            100                 105                 110

Ser Asn Lys His Cys Arg Gly Ser Thr Pro Arg Cys
        115                 120
```

<210> SEQ ID NO 3
<211> LENGTH: 27
<212> TYPE: DNA
<213> ORGANISM: Artificial Sequence
<220> FEATURE:
<223> OTHER INFORMATION: oligonucleotide primer
<400> SEQUENCE: 3

```
tttgctagaa acaagaagac ctacaat                                          27
```

<210> SEQ ID NO 4
<211> LENGTH: 27
<212> TYPE: DNA
<213> ORGANISM: Artificial Sequence
<220> FEATURE:
<223> OTHER INFORMATION: oligonucleotide primer
<400> SEQUENCE: 4

```
tttagcaact cgaagagcag aatcacc                                          27
```

<210> SEQ ID NO 5
<211> LENGTH: 37
<212> TYPE: DNA
<213> ORGANISM: Artificial Sequence
<220> FEATURE:
<223> OTHER INFORMATION: oligonucleotide primer
<400> SEQUENCE: 5

```
gctcgagatg aatttggtga atttccacag actgatc                               37
```